(12) United States Patent
Rigler

(10) Patent No.: US 8,009,888 B2
(45) Date of Patent: *Aug. 30, 2011

(54) MOBILE DEVICE FOR PARTICLE ANALYSIS BY IMAGE CORRELATION

(75) Inventor: Rudolf Rigler, St. Sulpice (CH)

(73) Assignee: Biophos AG, Wollerau (CH)

( * ) Notice: Subject to any disclaimer, the term of this patent is extended or adjusted under 35 U.S.C. 154(b) by 269 days.

This patent is subject to a terminal disclaimer.

(21) Appl. No.: 12/307,673

(22) PCT Filed: Jul. 16, 2007

(86) PCT No.: PCT/EP2007/006295
§ 371 (c)(1),
(2), (4) Date: Jan. 6, 2009

(87) PCT Pub. No.: WO2008/009403
PCT Pub. Date: Jan. 24, 2008

(65) Prior Publication Data
US 2009/0238423 A1 Sep. 24, 2009

Related U.S. Application Data

(60) Provisional application No. 60/831,227, filed on Jul. 17, 2006.

(51) Int. Cl.
*G06K 9/00* (2006.01)
*G01N 5/02* (2006.01)
*G01N 31/00* (2006.01)

(52) U.S. Cl. ........ 382/128; 382/100; 382/141; 356/336; 702/29

(58) Field of Classification Search .................. 382/100, 382/128, 141; 356/28, 27, 335, 336, 28.5; 708/250, 100, 200; 702/29, 71, 179; 73/861.06, 73/861; 250/200, 216, 573, 574; 386/263, 386/270

See application file for complete search history.

(56) References Cited

U.S. PATENT DOCUMENTS

| | | | |
|---|---|---|---|
| 5,627,642 A * | 5/1997 | Dhadwal et al. | 356/336 |
| 6,281,972 B1 * | 8/2001 | Ebara et al. | 356/336 |
| 6,587,200 B1 * | 7/2003 | Riebel et al. | 356/336 |
| 6,597,448 B1 * | 7/2003 | Nishiyama et al. | 356/237.4 |
| 6,697,517 B1 * | 2/2004 | Hunter | 382/149 |
| 6,873,725 B2 * | 3/2005 | Xu | 382/154 |
| 6,879,708 B2 * | 4/2005 | Wernet et al. | 382/107 |
| 7,558,813 B2 * | 7/2009 | Tanamoto et al. | 708/250 |
| 2003/0142291 A1 | 7/2003 | Padmanabhan et al. | |
| 2003/0194350 A1 | 10/2003 | Stamatelos et al. | |
| 2006/0000296 A1 | 1/2006 | Salter | |
| 2009/0238423 A1 * | 9/2009 | Rigler | 382/128 |

FOREIGN PATENT DOCUMENTS

| | | |
|---|---|---|
| GB | 2130718 A | 6/1984 |
| WO | 97/28737 A | 8/1997 |
| WO | 03/077552 A | 9/2003 |
| WO | 2006/074965 A | 7/2006 |

* cited by examiner

*Primary Examiner* — Sheela C Chawan
(74) *Attorney, Agent, or Firm* — Rothwell, Figg, Ernst & Manbeck, P.C.

(57) ABSTRACT

The present invention refers to a mobile device for measuring dynamic parameters of particles, e.g. spermatozoa, such as the translation speed and the rotational speed of particles.

16 Claims, 3 Drawing Sheets

MOBILE DEVICE FOR PARTICLE ANALYSIS BY IMAGE CORRELATION

CROSS REFERENCE TO RELATED APPLICATION

Figure 1:
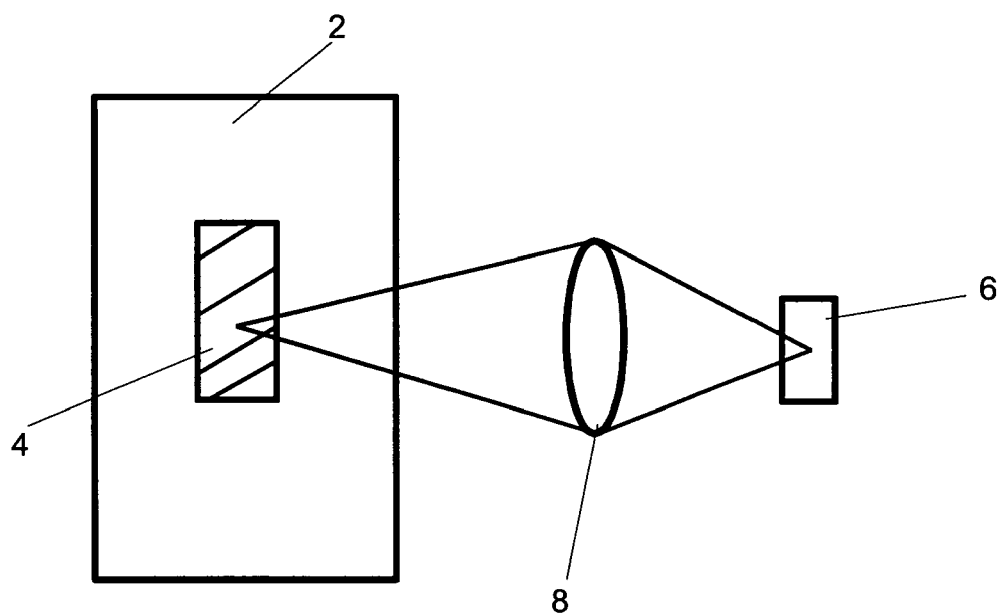

This application is a 35 U.S.C. 371 National Phase Entry Application from PCT/EP2007/006295, filed Jul. 16, 2007, which claims the benefit of U.S. Provisional Application No. 60/831,227 filed on Jul. 17, 2006, the disclosure of which is incorporated herein in its entirety by reference.

BACKGROUND OF INVENTION

The present invention refers to a mobile device for measuring dynamic parameters of particles, e.g. spermatozoa, such as the translation speed and the rotational speed of particles.

The present invention refers to a mobile device which is used for establishing parameters related to the dynamics/mobility of particles in a solution, in particular biological entities, e.g. cells and cell organelles including spermatozoa. Analysing the dynamic parameters and number of spermatozoa in semen is of importance in order to characterise spermatozoa, and constitutes an important tool for evaluation of male fertility.

By translation speed (velocity) is meant a directed motion of particles of one or more directions in a detection area or volume such that the path length is significantly longer that the observation length. In contrast to the translation speed there is e.g. Brownian motion signifying stochastic motion of the particles in all directions, i.e. the path length is significantly shorter than the observation length.

A method for determining the motility of spermatozoa is disclosed in U.S. Pat. No. 5,116,125, said analyser being based on dynamic laser light scattering.

Another method for measuring the motility of spermatozoa is to monitor the spermatozoa with a video camera and analyse the movements of the spermatozoa with computer based analysis of individual trajectories. Although this type of computer aided analysis generates fitness parameters rather quickly compared to manual testing, the analysis has several drawbacks particularly a significant variance with respect to the obtained parameters which increases with increased concentration of the spermatozoa.

PCT/EP2006/000369 discloses a device and a method for measuring concentration and mobility of particles, e.g. spermatozoa, by applying correlation analysis on fluctuation of the particles with respect to a detection area of a digital picture.

Object of the present invention is to provide a mobile device which allows a simple and rapid detection of dynamic parameters of particles in a solution.

Other advantages are apparent from the text below.

SUMMARY OF THE INVENTION

According to a first embodiment of the invention, there is provided a mobile device for measuring dynamic parameters of particles in a solution, characterised in that the device comprises a sample compartment, a light source, an image sensor for generating a digital picture, a computational unit for processing the digital picture from the image sensor and calculating the correlation function based on fluctuations of the particles with respect to detection areas of the digital picture, and a means for displaying the calculations results.

According to a further embodiment of the present invention, there is provided a mobile device for measuring dynamic parameters of particles in a solution, characterised in that the device comprises a sample compartment, a light source, an image sensor for generating a digital picture, means for transferring the digital picture to a remote computational unit for processing the digital picture and calculating the correlation function based on fluctuations of the particles with respect to detection areas of the digital picture, and a means for displaying the calculations results.

Still a further embodiment of the present invention refers to a method for measuring dynamic parameters of particles in a mobile device, characterised in that the method comprises
providing a sample fluid comprising particles in solution,
introducing the sample into a sample compartment suitable for measurement in a mobile device,
generating a digital picture of the sample in a mobile device,
processing the digital picture in a computational unit in the mobile device or in a remote computational unit by applying correlation analysis on fluctuation of the particles with respect to a detection area of the digital picture,
and displaying the result of the analysis in the mobile device.

The device and method are suitable for the analysis of mobile particles, including spermatozoa, bacteria, virus particles, or other mobile particles. Preferably, the invention is used for the analysis of spermatozoa.

The mobile device is a portable device having preferably a weight of less than about 1000 g, more preferably less than about 500 g. In an especially preferred embodiment, the mobile device comprises a mobile phone. The mobile device is preferably equipped with a digital photo and/or camera function. The mobile device preferably has an integrated light source and an imaging sensor for generating digital pictures, e.g. a two-dimensional detector matrix such as a CMOS detector or a CCD detector. The detector preferably has at least 1 megapixel, preferably at least 2 or 3 megapixels or higher, depending on the specific demands.

The mobile device may comprise an adaptor module fitted thereto for receiving the sample compartment and optionally an additional optical element, e.g. an optical focussing system, e.g. an additional lens. The sample compartment preferably is a one-way sample compartment which is removably mounted on the mobile device or the adaptor module.

In a first embodiment of the invention, the mobile device, e.g. the mobile phone, may be equipped with a computational unit for processing the digital pictures from the image sensor and calculating the correlation function. The calculated results can be displayed by the mobile device, e.g. by a LED display.

In a second embodiment, the mobile device comprises means for transferring the digital pictures to a remote computational unit. The transfer of the picture may be carried out by an online data transfer using e.g. a GSM/3G/GPRS connection to a remote computational unit which then calculates the image correlation function and their parameters. Preferably, the calculation is online. The calculated parameter values then may be transferred from the central computing unit to the mobile phone and displayed thereon. The pictures and/or the parameter values may be transferred as image files, e.g. as MMS files or in an equivalent format.

The parameters which may be obtained from the calculation of the correlation function may for example comprise the particle number, the mean particle velocity, the velocity distribution, the percentage of mobile and/or non-mobile particles, etc.

In a preferred embodiment, a sample fluid containing the particles to be determined is provided. The sample, e.g. spermatozoa in seminal plasma, may optionally be diluted with a suitable medium. The sample is positioned in a sample compartment preferably a one-way sample compartment which may be removably mounted on the mobile device. The content of the sample is imaged on an image sensor, e.g. on the pixel screen of a suitable detector, e.g. a CMOS detector or a CCD detector using the optical equipment of the mobile device with or without an additional optical element, e.g. an additional lens. Preferably, the sample imaged on the screen is magnified. The magnification depends on object and pixel sizes and preferably is in the order of about 5-20. Preferably, the measurement comprises the taking of an image sequence of 10-200, more preferably 50-100 individual images with a frame rate of e.g. 10-50 frames per second. The frames may be analysed by a computational unit integrated in the mobile phone or transferred to a remote computational unit, which then calculates the image correlation function and the desired parameters online. The resulting parameter values may be transferred from the remote computational unit to the mobile device.

The present invention also refers to methods for measuring the concentration and dynamic or mobility parameters of particles using the mobile device as described above. A first method comprising detecting events in a detection field, the events generated by the particles, and calculating time correlation function based on fluctuations of these events. A further method comprises applying correlation analysis on temporal fluctuations of the particles with respect to a detection area of a digital picture. Still a further method comprising detecting the particles by a detector capable of generating a digital picture, and applying correlation analysis based on temporal fluctuation of the particles with respect to a detection area of the digital picture. Yet another method comprises providing the particles in a solution, a light source, a detector capable of generating a digital picture, computational means, and applying correlation analysis, i.e. calculating the time correlation function or functions, based on temporal fluctuation of the particles with respect to a detection area of the digital picture.

In the present invention, fluctuations of events representing the particles of interest may be detected by a detection field. Preferably, temporal fluctuations of particles in a digital moving picture are analysed by using correlation analysis which generates a correlation function or correlation functions, said correlation function(s) giving information about dynamic parameters of the particles such as diffusion times, translation speed, rotational frequency, etc. and the number of particles in a volume element, i.e. the concentration. With the above mentioned dynamic parameters the mobility of the particles can be evaluated. Any particles or entities present in a solution can be evaluated according to the present invention with a size ranging from molecules to the macroscopic level. If the particles represent spermatozoa a number of important dynamic parameters can be calculated, such as swimming speed referred to as motility, rotational frequency and sperm concentration.

A novel feature of the present invention is to apply correlation analysis on fluctuation of particles present in a digital moving picture. The digital moving picture preferably consists of a plurality of individual images, e.g. $\geq 10$, preferably $\geq 50$ images. A digital moving picture of a solution containing the particles of interest is generated by inter alia using a suitable detector capable of generating a digital picture such as an image sensor connected to computational means. The digital picture may suitably by computational means be divided into several measurement/detection areas capable of generating adequate time dependent (temporal) fluctuation of the number of particles or concentration of the particles over the detection area boundary. Thus, the number of particles in the detection area is randomly changing around the average number. The fluctuation of the number of particles with respect to a detection area of the digital picture is analysed by the correlation function of the fluctuation signal, the signal representing the particles. Hence, the fluctuations are the basis for calculating a (time) correlation function or (time) correlation functions for generating the dynamic parameters and the number of the particles. Over time the particles will move in the digital picture, that is in-out motion across the detection area boundary. An image sensor of the present invention is a sensor capable of generating digital images of moving particles having a resolution in the image plane, i.e. in x- and y-axis, spatial resolution. As the image sensor generates a series of digital images (frames) having a resolution in time, a moving picture is obtained which is further analysed by applying correlation analysis. By the present invention dynamic parameters of particles in a solution can be evaluated at the same time as the digital images (the digital moving picture) are created, though, the method can also be applied on a digital moving picture stored on a suitable storage means.

The information on the digital picture generated by the image sensor stems from inter alia transmitted, scattered or emitted light from the particles. Normally, events not linked to the particles of interest are filtered away, suitably by using any type of digital imaging analysis. Having applied suitable imaging analysis tools to suppress the unwanted information from the image sensor, the time correlation function based on the registered fluctuation of the particles is calculated. In case there are several detection areas present in the digital image, several time correlation functions can be calculated simultaneously each correlation function generated from one and the same detection area.

The fluctuations of events and/or the number of particles in a detection area of the digital picture are monitored at a plurality of times ($\tau_1$, $\tau_2$, $\tau_3$, etc) during a specific time interval. The obtained time correlation function is basically a function describing the self similarity of events on a time scale, i.e. the detected particles are temporally correlated. Simplified, the time correlation function
G'($\tau$) is given by:

$$G'(\tau) = <I(t)*I(t+\tau)>$$

whereby the angular brackets $< \ldots >$ denote average over time, and possibly also over a plurality of detection areas, and I denotes the signal created by the detected particles.

Having calculated the correlation function, the concentration can be derived form the value of the correlation function at $\tau$=zero, which represent the inverse of the number of particles present in the detection area.

In case optical elements are positioned in the light beam between the object plane, i.e. sample compartment, and the image plane (plane of the image sensor) the digital picture will not only indicate particles located in an area element of the solution but all particles which are in focus. Hence, the digital picture gives information about a volume element of the sample, given inter alia by the focal depth (depth of filed) of the optical element(s).

In general terms the time correlation function G'($\tau$) normalised by the mean square intensity $<I^2>$ is related to the concentration and the mobility by:

$G(\tau)=1+1/N f(\text{mobility})]$.

With $G(\tau)=G'(\tau)/\langle I^2 \rangle$

In the above equation, the amplitude term 1/N depends on the inverse number of particles per volume element N and on a function f(mobility) which describes translational as well as rotational motion. As revealed by fluctuation theory, fluctuations increase with a decreasing average particle number.

The fluctuation of the events and/or the particles in the digital picture during the relevant time frame should be of such a magnitude that an accurate time correlation function can be calculated. Hence, the detection area or detection areas of the digital picture must be dimensioned such that proper fluctuation across the detection area boundary is achieved. Generally, higher fluctuation generates better time correlation function. The digital moving picture is suitably divided into a plurality of detection areas which all can have identical or varying size and shape.

Assume that by computational means the digital picture is divided into a plurality, preferably $\geq 10$, e.g. 100 detection areas, each area representing several pixel elements of the image sensor. At several times $\tau_1, \tau_2$, etc. (i.e. image frames at times $\tau_1, \tau_2$, etc.) during a time interval the intensities $I_1, I_2$, etc. representing the particles of interest from the detection area $A_1$ are used for calculating the correlation function $G_1$ with respect to area $A_1$. Simultaneously another 99 correlation functions are calculated $G_2$ up to $G_{100}$. Having several correlation functions the average correlation function can easily be established.

The digital picture is preferably generated by a detector capable of generating a digital picture, such as an image sensor. Any sensor/detector capable of generating a digital output which can be used to extract dynamic parameters of moving particles by applying inter alia correlation analysis on the digital output is suited for the present invention. The picture might be captured and stored in an analog format and subsequently be transformed to a digital format which is then processed using correlation analysis. By digital picture is meant a digital moving picture suitably obtained by a multitude of time resolved images, i.e. image frames. The image sensor is characterised by the capability of rapid image capturing, generating digital images ready for computer analysis, having spatial and temporal resolution, and high sensitivity to a whole spectrum of detected light. Suitable image sensors are sensors, which may be incorporated into a mobile device, e.g. solid state image sensors/detectors. Solid state type image sensors are especially preferred. A solid state image sensor is a silicon chip comprising a multitude of photosensitive diodes referred to as photosites. In the short instant that the shutter is open each pixel records the intensity or brightness of the light falling on said pixel by accumulating a charge. The time resolved images of the digital picture contain a high number of picture elements or pixels, usually a few microns in size, where each pixel corresponds to a photosite of the image sensor. Accordingly, the resolution of the image is to a large extent given by the number of photosites on the image sensor. The resolution of the image sensor is not an important factor for the present invention and can vary within a wide range from about one thousand up to about 20 million. A higher resolution of the image sensor may be favourable.

The most common solid state image sensors are charge coupled devices (CCD) and complementary metal oxide semiconductor detectors (CMOS). Both classes of solid state image sensors are silicon semiconductors designed to capture photons and convert them into electrons. CCD and CMOS image sensors are similar with respect to basic design, but differ in terms of how the charges (electrons) of the photosites are extracted from the sensor. If high sensitivity is needed CMOS avalanche photodiode image sensors can be used.

Solid state image sensors, e.g. silicon photodiodes, are sensitive to light in a wide spectral range of from about 200 nm up to about 1200 nm.

The resolution of the digital image is basically governed by the resolution of the image sensor, thus, each pixel of the image sensor represents one pixel in the digital image. However, the resolution can also be improved by software adding pixels to the digital image. By introducing optical means, e.g. one or more optical elements such as lens systems including objectives and oculars, the particles in the solution can be magnified. Thus, the particles in the image plane (plane of image sensor) are magnified with respect to the physical particles positioned in the object plane. However, the optical means may also have the properties to make the particles in the plane of the image smaller that in the object plane. Such an arrangement might be considered if the particles have a projected area similar to the total area of the image sensor. The smallest detection area of the digital picture/image is given by an area of the image representing an individual pixel element of the image sensor up to in principle an area comprising all pixel elements. Typically, the size/shape of a detection area or areas of the digital picture is/are larger that the projected area of the particles of interest in the digital picture. The analysed volume within the sample is inter alia given by the optical means applied. The optical means can suitably be a microscope setup, such as a compound microscope comprising an objective and a projection lens having a light source rendering transmitted, scattered or emitted light having a wavelength matching the image sensor. When having optical means, i.e. optical elements, in the light path between the object plane and the image plane (image sensor), the analysed volume within the sample is in principle given by the objective and its magnification, both restricting the volume in radial direction with respect to the light path.

Furthermore, by the focal depth of the optical means the measurement volume is in principal restricted in axial direction.

The source of light can be of any wavelength as long as the energy of the electromagnetic radiation does not significantly influence the particles to be analysed and can be detected by the image sensor. The light can have a wide range of wavelengths such as visible light, e.g. wavelengths from about 200 nm up to about 1200 nm, or have a narrower range of wavelengths down to monochromatic light. Either the light source emits monochromatic light or light having a narrow wavelengths, alternatively, suitable filters, i.e. monochromatic filters, are applied if the source of light has a wider range of wavelengths. Also light sources producing coherent light, suitably monochromatic, can preferably be used, Examples of coherent light sources are laser light sources. Suitable light sources are inter alia xenon, high and low pressure mercury, tungsten, halogen light sources, light emitting diodes (LED) such as blue diodes, lasers and laser diodes. For the analysis of certain types of motion (rotational motion) it is an advantage if the lights is polarised. To choose a specific type of illumination is not important to the present invention, hence, any illuminating type can be applied as long as an accurate time correlation function can be generated.

If emitted light from the particles, e.g. fluorescence, is captured by the image sensor, optical means in the light path between the object plane and the image plane are usually fitted including additional filters in addition to a microscope, in order to separate the excitation light from the emitted light. With an incident light fluorescence microscope, the sample is illuminated with excitation light through the objective lens. A dichroic beam splitter placed in the optical path between the objective and the image sensor, transmits or reflects light depending on the wavelength. The light source used for excitation is commonly a laser. Any laser can be used which is capable of exciting the fluorescent particles of interest including e.g. argon- or argon krypton lasers, single-line He—Ne lasers, laser diodes, etc. If larger volume elements of excitation are sufficient, also non-coherent light sources as mercury high pressure lamps or halogen lamps can be used. If fluorescence is detected it is preferred to have a favourable signal to noise ratio. Fluorescence which is out of focus appears as flares and reduces the signal significantly. Hence, the measurement volume within the sample, in principle given by the aperture and its magnification of the objective in radial direction, is also restricted in axial direction. This restriction of the volume in axial direction is preferably obtained by applying an aperture (pin-hole), which is conjugated to the object and the image plane. However, the image sensor consisting of individual photosites (pixels) per se can also function as an aperture and detector provided the detector is localised in the image plane conjugate to the object plane. The incident epi illuminescent fluorescence microscope is preferred if the particles analysed are small with a molecular weight of below 100 000 mega Daltons. Examples of such small particles are biomolecules such as vesicles or cell organelles. In addition, the volume element has suitable a volume from about $10^{-16}$ liter up to about $10^{-10}$ liter, preferably from about $10^{-15}$ up to about $10^{-12}$. In order to obtain these small measurement volumes, the numeric aperture of the objective is suitably above about 0.7, more preferably above 1.0.

Furthermore, in case fluorescence is measured specific properties related to the expression of specific gene products such as surface proteins, which are important for fertilization processes and/or with other important functional properties can be calculated by using fluorescence intensity fluctuation analysis. In addition, the percentage of spermatozoa in relation of the total sperm count as well as the specific expression level (expressed molecules per spermatozoa) can be measured. Similarly, even the nucleic acid content can be analysed.

The original light source may preferably be divided into a plurality of light sources which is obtained by positioning a diffractive optical element in the beam path. The number of individual beam paths is preferably matched by an equal number of detection areas in the digital picture.

The sample compartment can have a wide variety of shapes both closed as well as open as long as the characteristic of the particle solution is not significantly changed over time. Preferably, the sample holding means is fitted with means for keeping the temperature at a specific level. To keep the solution at a predetermined temperature can be of importance if biological systems are analysed, e.g. spermatozoa. Preferably, the size of the sample container in the direction of the light path equals or is smaller than the focal depth of the optical means, provided optical means are situated in the light path between the sample container and the image sensor. Preferably, the sample container can be removably mounted on the mobile device or an adaptor module fitted to be connected to the mobile device.

The mobile device according to the present invention can have more than just a detector capable of generating a digital picture (e.g. different detector types such as a CCD type or CMOS type sensor) especially if emitted light from the particles such as fluorescence is to be captured. A second detector is suitably adapted to capture phenomena with short response time, e.g. a detector having a high sensitivity such as an avalanche photo diode (APD) detector, e.g. a CMOS APD detector. Having two or more detectors, at least one other beam splitter is located in the beam path.

By using diffractive optical means the light source can be divided into a plurality of light sources generating a plurality of measurement volumes. The dynamic parameters of the particles present in each volume element can be calculated by applying an image sensor having a number of measurement fields suitably corresponding to the number of generated light sources by a diffractive optical element. A suitable position sensitive detector can be any of those mentioned above. The diffractive optical element is suitably positioned between the light source and the beam splitter.

Spermatozoa, or semen, can be measured by the present invention. The fitness of the spermatozoa is given by the swimming speed and rotation frequency, also the concentration can be calculated as the number of sperms is given by the amplitude of the correlation function at $\tau$=zero. The total concentration of spermatozoa includes also dead or immobile spermatozoa, the number of which within a detection field can also be measured by rendering them mobile to the detection system by moving the detection field, either mechanically or computationally. Furthermore, by using an image sensor also a visual image is generated of the spermatozoa. The spermatozoa may also be labelled by fluorescent dye or dye conjugated markers, e.g. antibodies with specificity for certain properties of spermatozoa, e.g. DNA, surface based receptors, proteins related to the head, mid-piece or tail of the spermatozoa. Fluorescent labelling of spermatozoa is usually performed by binding of fluorescent markers, e.g. antibodies to the spermatozoa which is known to the person skilled in the art. Suitable fluorescent dyes are those having the absorption maxima in the visible spectrum. i.e. from 350 nm to 750 nm, exemplified by rhodamines such as rhodamine green, TMR, rhodamine B and 6G, cyanines like Cy2, Cy3 and Cy5, texas red. In order to visualise (create specific emission) nucleic acids like DNA, the gene material, dyes interacting specifically with DNA such as ethidium bromide, propidium iodide, acridin dyes and other nucleic specific molecules (e.g. gene probes) can be used.

According to one embodiment of the invention, the device comprises a phase contrast compound microscope and an image sensor such as a CCD or a CMOS detector. When spermatozoa/semen is measured the total magnification of the image (object versus intermediate image) suitably is in the range of from about 10 to about 30 times. Thus, the head of a sperm measuring approx. 3 µm would in the intermediate image plane have a size from 30 µm to 90 µm. The image sensor is suitably positioned in the plane of the intermediate image. The digital image of the image sensor is divided into a plurality of separate detection areas. The detection area can preferably have a size which is equal or greater than the size of the particles in the digital image suitably up to an area giving sufficient fluctuations of the number of particles for calculating accurate dynamic parameters using correlation analysis. The shape of the detection area is not important as long as an accurate correlation function can be calculated. The area can have any shape, e.g. circular or rectangular. The image sensor is furthermore connected to computational means comprising suitable software and hardware for video image analysis. With the computer screen a digital moving picture of the sample is generated. By applying appropriate image analysis, noise, e.g. background such as different categories of non-relevant particles, can be filtered away such that only the fluctuation of the relevant particles form the basis for the calculation of the correlation function. Furthermore, the registering of particles by the image sensor and the calculation of the time correlation function is performed essentially simultaneously.

For further details it is referred to the disclosure of PCT/EP2006/000369, the content of which is herein incorporated by reference.

FIGURES

FIG. 1 shows a first embodiment of a mobile device, e.g. a mobile phone according to the present invention. The mobile device (2) comprises a detector (4), e.g. a CMOS or a CCD detector. Mounted on the mobile device is a sample compartment (6) comprising an optical element (8), e.g. a lens.

Figure 2:
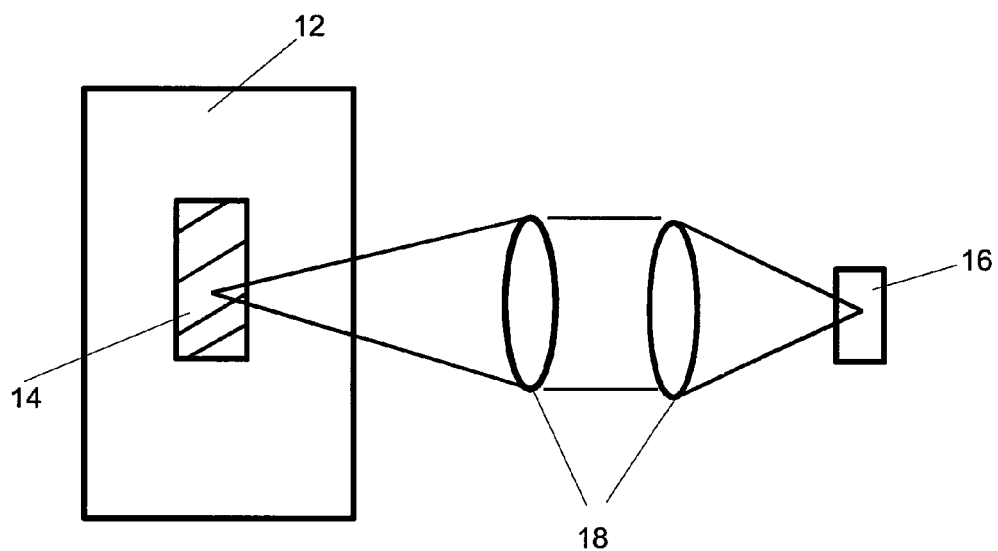

In FIG. 2, a mobile device (12) with a detector (14) is shown. The sample compartment (16) is mounted on the device and comprises an optical element (18) which is a lens array.

Figure 3:
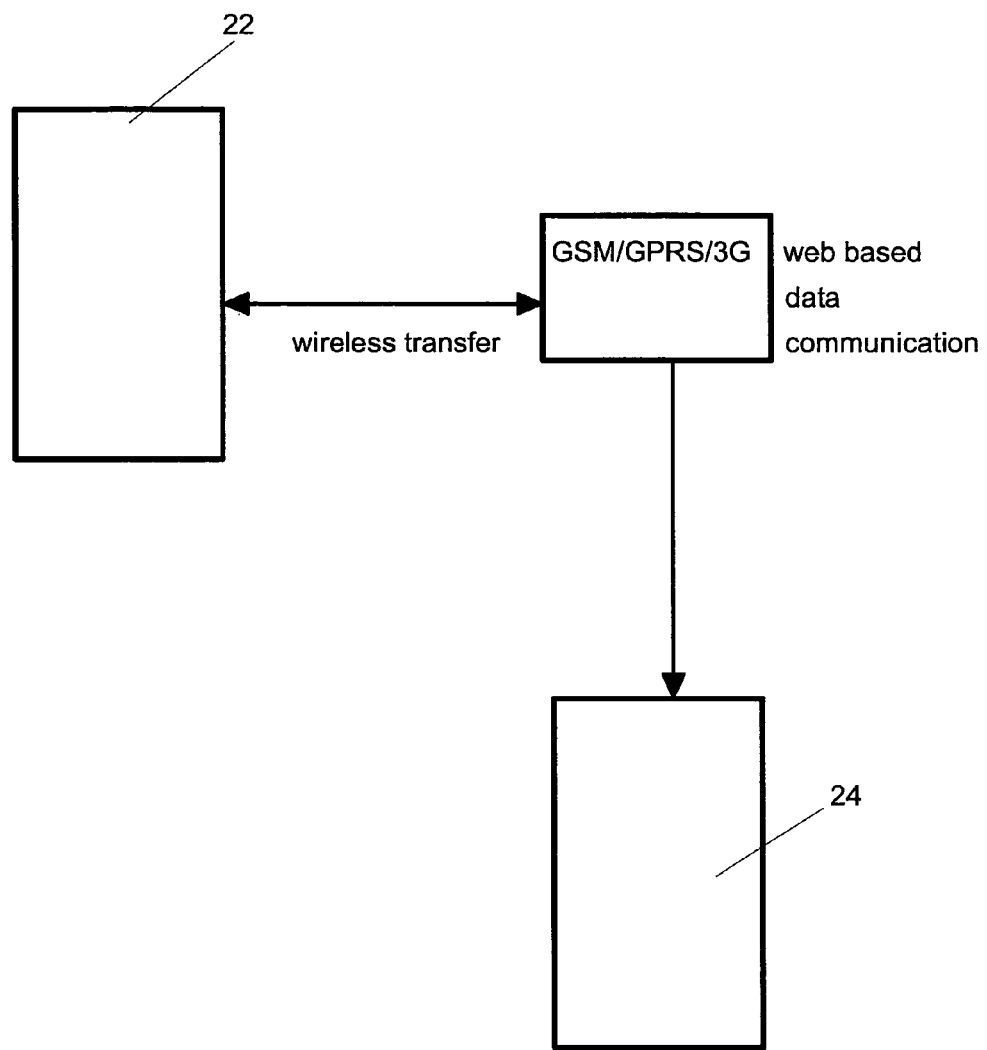

FIG. 3 is a schematic depiction of the communication between the mobile device (22) via wireless transfer by means of GSM/GPRS/3G web-based data communication with a remote computational unit (24).

The invention claimed is:

1. A mobile device for measuring dynamic parameters of particles in a solution, the device comprises a sample compartment, a light source, an image sensor for generating a digital picture, a computational unit for processing the digital picture wherein the parameters are obtained by applying correlation analysis on temporal fluctuations of the number of particles with respect to a detection area of the digital picture, and that a time correlation function of functions is/are calculated based on the temporal fluctuations of the number of particles, and a means for displaying the calculations results.

2. The device of claim 1, wherein the device is a mobile phone.

3. The device of claim 1 comprising an adapter module fitted thereto, wherein the adapter module comprises the sample compartment and optionally an additional optical element.

4. The device of claim 1, wherein the sample compartment is a one-way sample compartment which is removably mounted on the mobile device or the adapter module.

5. The device of claim 1, wherein the light source is an integrated mobile phone flash light source.

6. The device of claim 1, wherein the image sensor is a CCD detector or a CMOS detector.

7. A mobile device for measuring dynamic parameters of particles in a solution, the device comprising a sample compartment, a light source, an image sensor for generating a digital picture, means for transferring the digital picture to a remote computational unit for processing the digital picture, wherein the parameters are obtained by applying correlation analysis on temporal fluctuations of the number of particles with respect to a detection area of the digital picture, and that a time correlation function of functions is/are calculated based on the temporal fluctuations of the number of particles; and a means for displaying the calculations results.

8. A method for measuring dynamic parameters of particles in a mobile device, wherein the method comprises:
   providing a sample fluid comprising particles in solution,
   introducing the sample into a sample compartment suitable for measurement in a mobile device,
   generating a digital picture in a computational unit in the mobile,
   processing the digital picture in a computational unit in the mobile phone or in a remote computational unit by applying correlation analysis on temporal fluctuations of the number of particles with respect to a detection area of the digital picture, and that a time correlation function of functions is/are calculated based on the temporal fluctuations of the number of particles; and displaying the results of the analysis in the mobile phone.

9. The method according to claim 8, characterised in that the moving digital picture is generated by an image sensor.

10. The method according to claim 8, characterised in that the correlation function is based on fluctuations of particles with respect to a plurality of detection areas.

11. The method according to claim 8, characterised in that the image sensor is a CCD detector or a CMOS detector.

12. The method according to claim 8, wherein the method further comprises background subtraction.

13. The method according to claim 8, wherein the particles are spermatozoa.

14. The method of claim 8, wherein the moving digital picture comprises a picture sequence of a plurality of several images, preferably at least 10 images.

15. The method of claim 8, wherein the picture sequence is generated within a time of 0.5-1 0 sec, preferably 1-2 sec.

16. The method of claim 8, wherein the mobile device comprises a sample compartment, a light source, an image sensor for generating a digital picture, a computational unit for processing the digital picture wherein the parameters are obtained by applying correlation analysis on temporal fluctuations of the number of particles with respect to a detection area of the digital picture, and that a time correlation function of functions is/are calculated based on the temporal fluctuations of the number of particles, and a means for displaying the calculations results.

* * * * *